United States Patent
Kamani et al.

(10) Patent No.: US 12,006,324 B1
(45) Date of Patent: Jun. 11, 2024

(54) PREPARATION METHOD OF TRILACICLIB AND PRECURSORS OF TRILACICLIB

(71) Applicant: Chunghwa Chemical Synthesis & Biotech Co. Ltd., New Taipei (TW)

(72) Inventors: Satyanarayana Kamani, New Taipei (TW); Hsin-Yun Chang, New Taipei (TW); Tzu-Chiang Lu, New Taipei (TW); Chin-Cheng Mai, New Taipei (TW)

(73) Assignee: CHUNGHWA CHEMICAL SYNTHESIS & BIOTECH CO. LTD., New Taipei (TW)

( * ) Notice: Subject to any disclaimer, the term of this patent is extended or adjusted under 35 U.S.C. 154(b) by 0 days.

(21) Appl. No.: 18/084,179

(22) Filed: Dec. 19, 2022

(30) Foreign Application Priority Data

Dec. 15, 2022 (TW) .................................. 111148203

(51) Int. Cl.
*C07D 487/14* (2006.01)

(52) U.S. Cl.
CPC .................................. *C07D 487/14* (2013.01)

(58) Field of Classification Search
CPC ...................................................... C07D 487/14
USPC ........................................................... 514/250
See application file for complete search history.

(56) References Cited

U.S. PATENT DOCUMENTS 10,865,210 B2   12/2020   Smith et al.

FOREIGN PATENT DOCUMENTS

CN   113788837 A   12/2021

*Primary Examiner* — Taofiq A Solola
(74) *Attorney, Agent, or Firm* — Muncy, Geissler, Olds & Lowe, P.C.

(57) ABSTRACT

Disclosed herein is a specific method of preparation of Trilaciclib. The said method is to provide an efficacy of a protection free synthetic method of Trilaciclib with less steps and good yields.

21 Claims, No Drawings

PREPARATION METHOD OF TRILACICLIB AND PRECURSORS OF TRILACICLIB

FIELD OF THE INVENTION

The present invention relates to a preparation method of Trilaciclib, to compounds of formulae (II), (III) and (IV), which are precursors of Trilaciclib.

BACKGROUND OF THE INVENTION

Trilaciclib dihydrochloride is an active ingredient in COSELA which was approved for commercial sale by the Food and Drug Administration (FDA) on Feb. 12, 2021 as a new CDK4/6 inhibitor. Cosela was assigned to the G1 Therapeutics company, a drug that reduced the myelosuppression that occurs in patients with extensive small cell cancer who received some type of chemotherapy, and a first CDK4/6 inhibitor approved for this indication. Cosela quickly arrests normal cells to prevent chemotherapy-induced myelosuppression and may improve tumor efficacy. Trilaciclib is used as a myelopreservation agent to protect healthy cells, notably hematopoietic cells, during chemotherapy.

U.S. Pat. No. 10,865,210B2 has disclosed a synthesis process of Trilaciclib hydrochloride salt. The synthesis of Trilaciclib included using 4-chloro-2-methylthio pyrimidine-5-carboxylic acid ethyl ester as a staring material, and then conducting nucleophilic substitution, Boc protection of an amide group, intramolecular cyclization, Tf protection of a phenolic hydroxyl group, reductive elimination of OTf group, thioether oxidation, Boc deprotection and nucleophilic substitution of 1-methyl-4-(6-aminopyridin-3-yl)piperazine in presence of strong alkali to obtain a final product Trilaciclib.

CN113788837 describes the synthesis of Trilaciclib with condensation of 2-(methylthio)-7H-pyrrole [2,3-d] pyrimidine-6-carboxylic acid and 1-aminomethyl-1-cyclohexanol, cyclization fallowed by nucleophilic substitution.

SUMMARY OF THE INVENTION

The inventors of the present application found that the synthesis of Trilaciclib with existing technology often results in poor yields due to excessive synthesis steps of the protection/deprotection process.

Accordingly, the present invention provides a method for preparing Trilaciclib of formula (I), comprising:

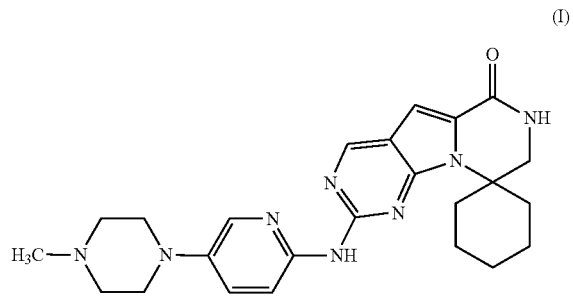 [SMILES: CN1CCN(c2ccc(Nc3ncc4cc5n(c4n3)C3(CCCCC3)CNC5=O)nc2)CC1]

(a) oxidizing a compound of formula (VII) to afford a compound of formula (VI-1) or (VI-2);

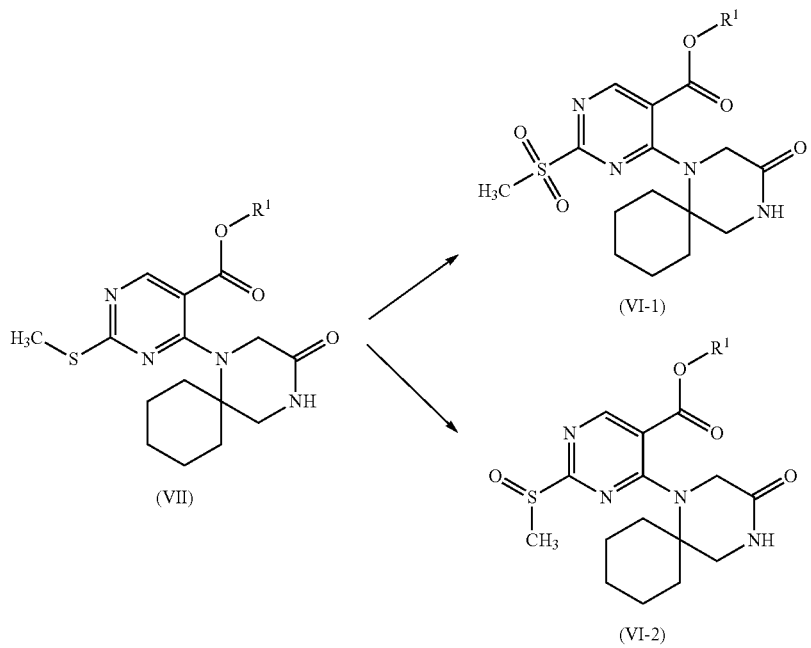

(b) reacting a compound of formula (V) and the compound of formula (VI-1) or

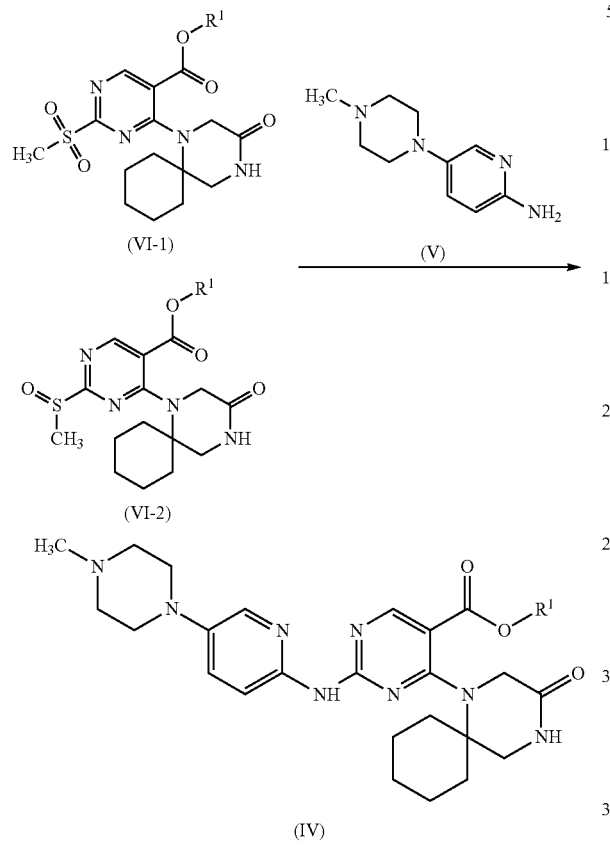

(c) conducting an intramolecular cyclization of the compound of formula (IV) in presence of base to afford a compound of formula (III);

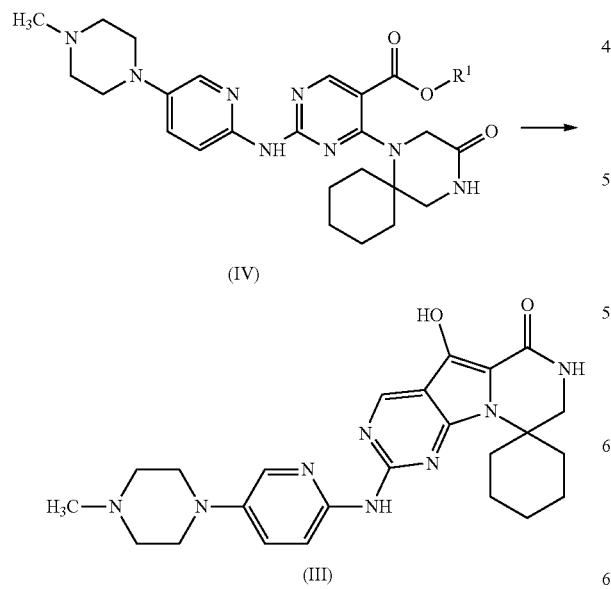

(d) activating a hydroxyl group of the compound of formula (III) to become a leaving group to afford a compound of formula (II);

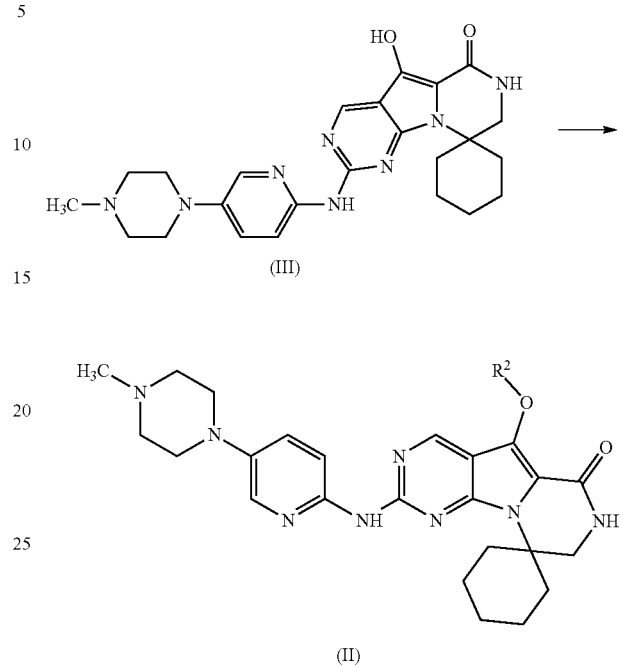

(e) conducting a reductive elimination of the compound of formula (II) to afford Trilaciclib;

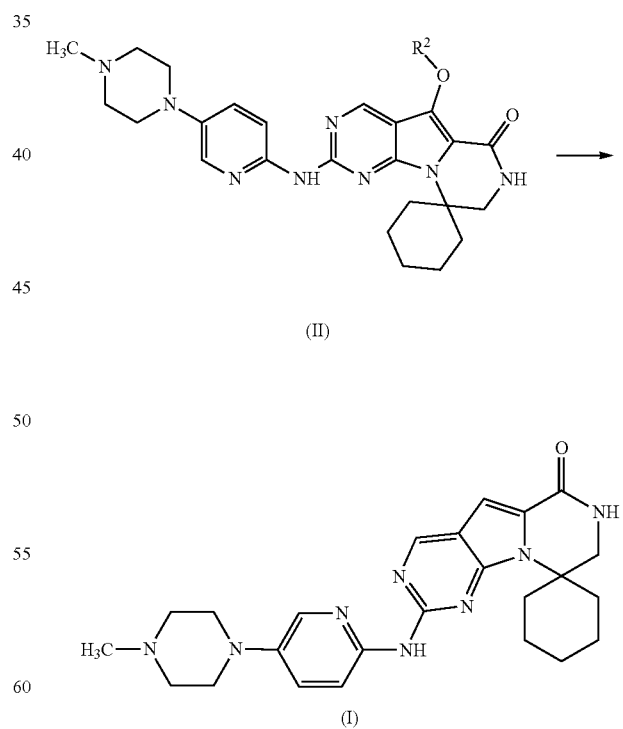

wherein $R^1$ is selected from hydrogen or C1~C4 alkyl, aryl; $R^2$ is selected from hydrogen, silyl, halo alkyl, —C(O) alkyl, —S(O)$_2$ alkyl, —S(O)$_2$ halo alkyl, —S(O)$_2$ aryl or —S(O)$_2$ aryl-alkyl.

In some embodiments, the oxidizing agent used in the step (a) is selected from the group consisting of oxone, hydrogen peroxide, meta-chloroperoxybenzoic acid, sodium hypochlorite and sodium chlorite.

In some embodiments, the solvent used in the step (a) is selected from the group consisting of acetonitrile, tetrahydrofuran, dimethylformamide, dimethyl sulfoxide, water and dioxane.

In some embodiments, the step (a) is carried out at a temperature of −20 to 80° C.

In some embodiments, the strong alkali in the step (b) is alkali metal hexamethyldisilazane.

In some embodiments, the alkali metal hexamethyldisilazane is selected from a group consisting of lithium hexamethyldisilazane, sodium hexamethyldisilazane and potassium hexamethyldisilazane.

In some embodiments, the solvent used in the step (b) is selected from a group consisting of tetrahydrofuran, 1,4-dioxane and toluene.

In some embodiments, the step (b) is carried out at a temperature of −40 to 60° C.

In some embodiments, the equivalent of alkali metal hexamethyldisilazane of the step (b) is 1.0 to 20.0 equiv.

In some embodiments, the base used in the step (c) is selected from a group consisting of lithium hydroxide, sodium hydroxide, magnesium hydroxide, aluminum hydroxide, sodium methoxide, N,N-diisopropylethylamine, dimethylol propionic acid, 1,4-diazabicyclo[2.2.2]octane, triethylamine, 1,8-diazabicyclo[5.4.0]undec-7-ene, potassium tert-butoxide and sodium tert-butoxide.

In some embodiments, the intramolecular cyclization in the step (c) is carried out at a temperature of 50 to 100° C.

In some embodiments, the reagent used to activate the hydroxyl group in the step (d) is selected from the group consisting of p-toluensulfonyl chloride, p-toluensulfonyl anhydride, trifloromethane sulfonylchloride, trifloromethane sulfonic anhydride, methane sulfonyl chloride and methane sulfonyl anhydride.

In some embodiments, the equivalent of the reagent is 1.0 to 20 equiv.

In some embodiments, the solvent used in the step (d) is selected from a group consisting of dichloromathane, dimethylformamide, acetonitrile and tetrahydrofuran.

In some embodiments, the activation of hydroxyl group in the step (d) is carried out at a temperature of −20 to 90° C.

In some embodiments, the reductive elimination in the step (e) is carried out in presence of a palladium catalyst with a reducing agent.

In some embodiments, the palladium catalyst is selected from a group of 10% Pd/C, tetrakis(triphenylphosphine) palladium (0), palladium acetate, palladium chloride, trans-dichlorobis(acetonitrile)palladium (II), 1,1-bis(diphenylphosphino)ferrocene)dichloropalladium-dichloromethane (1:1), 1,1'-bis(diphenylphosphino)ferrocene)dichloropalladium, tris(dibenzyllideneacetone)dipalladium, and bis(triphenylphosphine)palladium (II) dichloride.

In some embodiments, the reducing agent is selected from a group consisting of hydrogen gas, triethyl silane, trimethyl silane, ammonium formate and formic acid.

In some embodiments, the solvent used in the step (e) for the reductive elimination is selected from a group consisting of alcohols, ethers and esters.

The present invention further provides a compound of formula (II),

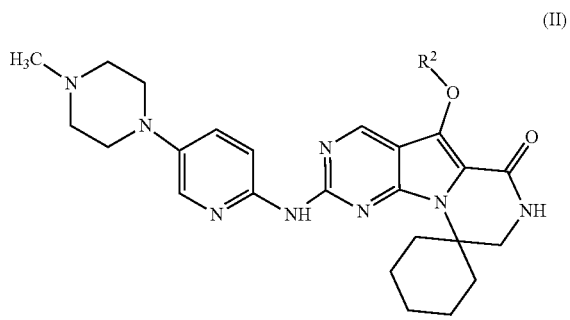

wherein $R^2$ is selected from hydrogen, silyl, halo alkyl, —C(O) alkyl, —S(O)$_2$ alkyl, —S(O)$_2$ halo alkyl, —S(O)$_2$ aryl or —S(O)$_2$ aryl-alkyl.

The present invention further provides a compound of formula (III).

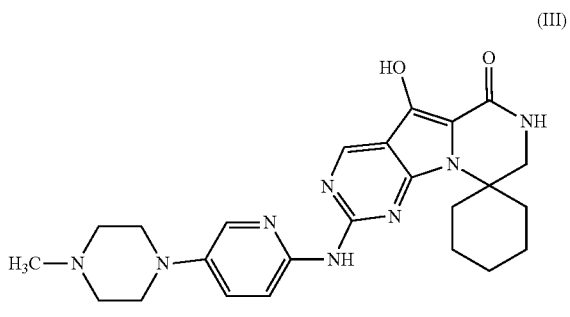 [SMILES: CN1CCN(c2ccc(Nc3ncc4c(O)c5n(c4n3)C3(CCCCC3)CNC5=O)nc2)CC1]

The present invention further provides a compound of formula (IV),

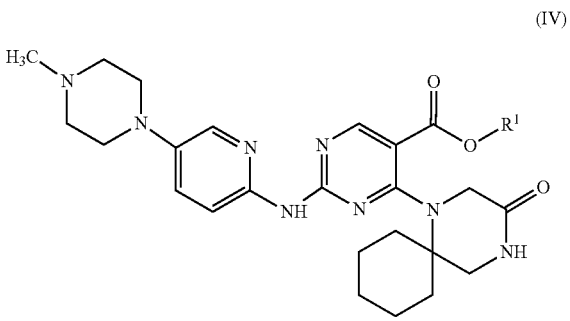

wherein $R^1$ is selected from hydrogen or C1~C4 alkyl, aryl.

Accordingly, the effect of the present invention is to provide a protection free synthesis of Trilaciclib with less steps and good yields. In addition, new precursors such as the compounds of the above formula (II), (III) and (IV) of Trilaciclib are also provided.

DETAILED DESCRIPTION OF THE INVENTION

Definition

The terms used in this specification are generally within the scope of the present invention and the specific context of each term has its usual meaning in related fields. The specific terms used to describe the present invention in this specification will be described below or elsewhere in this specification, so as to help people in the industry understand the relevant description of the present invention. The same term has the same scope and meaning in the same context. In addition, there is more than one way to express the same thing; therefore, the terms discussed in this article may be replaced by alternative terms and synonyms, and whether a term is specified or discussed in this article does not have any special meaning. This article provides synonyms for certain terms, but the use of one or more synonyms does not mean that other synonyms are excluded.

The terms "a" and "an" do not denote a limitation of quantity, but rather denote the presence of at least one of the referenced items. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

Compounds are described using standard nomenclature. Unless defined otherwise, all technical and scientific terms used herein have the same meaning as is commonly understood by one of skill in the art to which this invention belongs.

The compounds in any of the Formulas described herein include racemates, enantiomers, mixtures of enantiomers, diastereomers, mixtures of diastereomers, tautomers, N-oxides, isomers; such as rotamers, as if each is specifically described.

As used herein, a dash ("-") that is not between two letters or symbols is used to indicate a point of attachment for a substituent. For example, —(C═O)NH$_2$ is attached through carbon of the keto (C═O) group.

As used herein, the terms "alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is C1~C2, C1~C3, or C1~C6. The specified ranges as used herein indicate an alkyl group having each member of the range described as an independent species. For example, the term C1~C6 alkyl as used herein indicates a straight or branched alkyl group having from 1, 2, 3, 4, 5, or 6 carbon atoms and is intended to mean that each of these is described as an independent species. For example, the term C1~C4 alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane.

As used herein, the terms "carbocyclyl", "carbocyclic", "carbocycle" or "cycloalkyl" is a saturated or partially unsaturated (i.e., not aromatic) group containing all carbon ring atoms and from 3 to 14 ring carbon atoms ("C3~14 carbocyclyl") and zero heteroatoms in the non-aromatic ring system. In some embodiments, a carbocyclyl group has 3 to 10 ring carbon atoms ("C3~10 carbocyclyl").

As used herein, the term "halo alkyl" indicates both-branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and pentafluoroethyl.

As used herein, the terms "halo" or "halogen" indicates independently any of fluoro, chloro, bromo or iodo.

As used herein, the term "amino" is —NH$_2$.

As used herein, the term "aryl" refers to a radical of a monocyclic or polycyclic (e.g., bicyclic or tricyclic) 4n+2 aromatic ring system (e.g., having 6, 10, or 14n electrons shared in a cyclic array) having 6~14 ring carbon atoms and zero heteroatoms provided in the aromatic ring system ("C6~14 aryl"). For example, an aryl group has 6 ring carbon atoms ("C6 aryl"; e.g., phenyl). For example, an aryl group has 10 ring carbon atoms ("C10 aryl"; e.g., naphthyl such as 1-naphthyl and 2-naphthyl). For example, an aryl group has 14 ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2 or 3 heteroatoms independently selected from nitrogen, oxygen, phosphorus, sulfur, silicon or boron, to form, for example, a 3,4-methylenedioxyphenyl group. For example, aryl groups are pendant. An example of a pendant ring is a phenyl group substituted with a phenyl group.

As used herein, the term "aryl-alkyl" is an aryl group as defined herein attached through an alkyl group.

As used herein, the terms "alkylsulfinyl", "alkyl sulfoxide" or "—S(O) alkyl" as defined herein are represented by

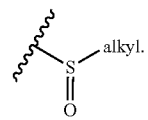

As used herein, the terms "alkylsulfonyl", "alkyl sulfone" or "—S(O)₂ alkyl" as defined herein are represented by

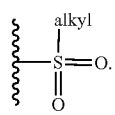

As used herein, the term "silyl" means "—SiH₃."

As used herein, the term "room temperature" refers to a temperature in the range of 25 to 35° C.

In one aspect, the present invention provides a method for preparing Trilaciclib of formula (I), comprising:

(I)

(a) oxidizing a compound of formula (VII) to afford a compound of formula (VI-1) or (VI-2);

(b) reacting a compound of formula (V) and the compound of formula (VI-1) or (VI-2) under strong alkali to afford a compound of formula (IV);

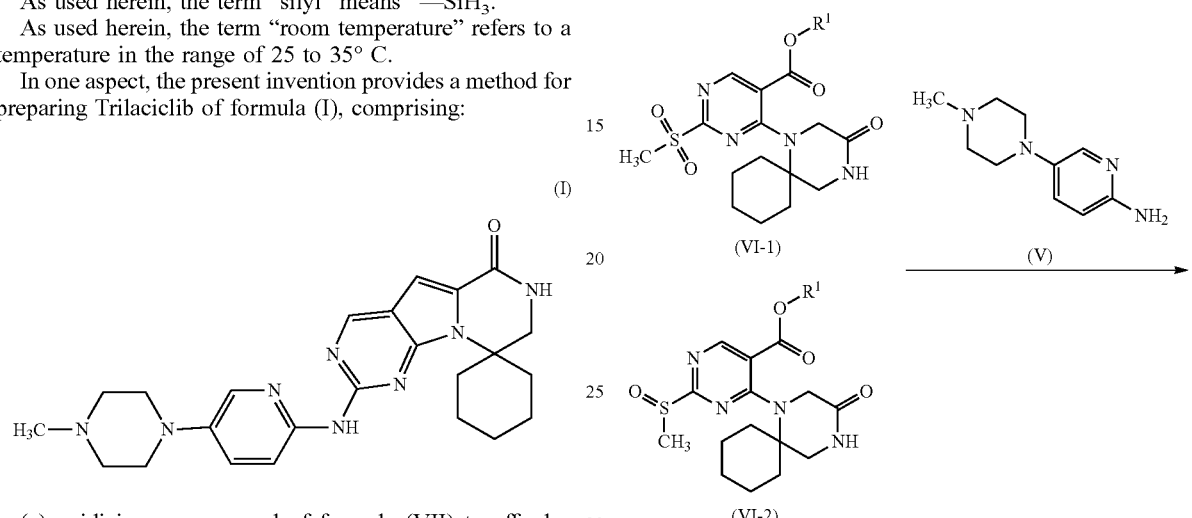

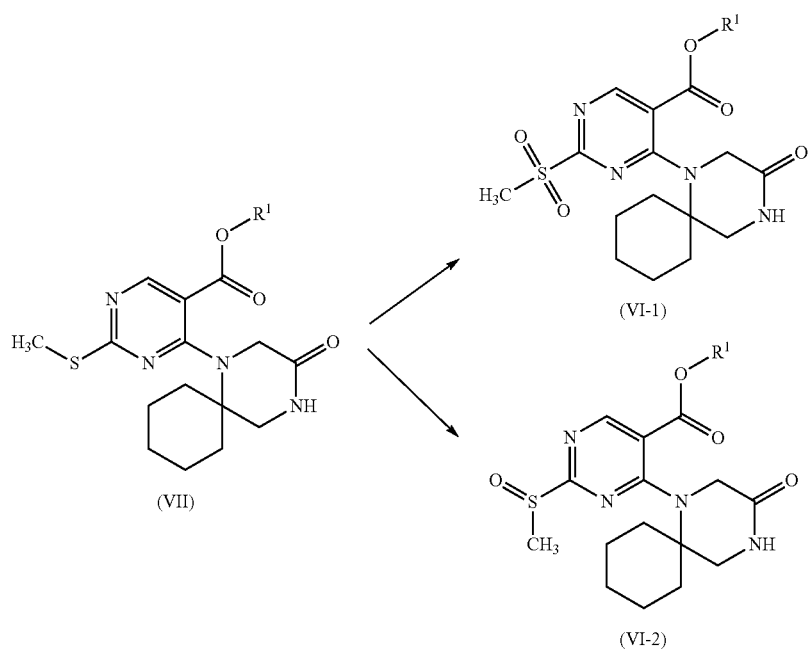

-continued

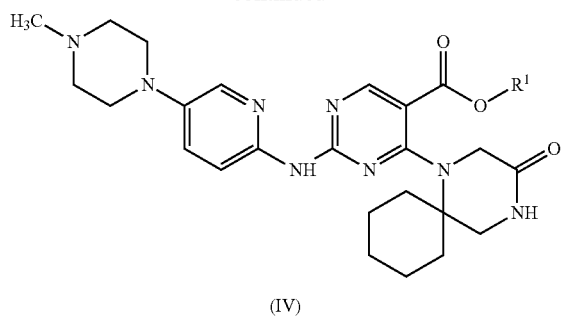

(IV)

(c) conducting an intramolecular cyclization of the compound of formula (IV) in presence of base to afford a compound of formula (III);

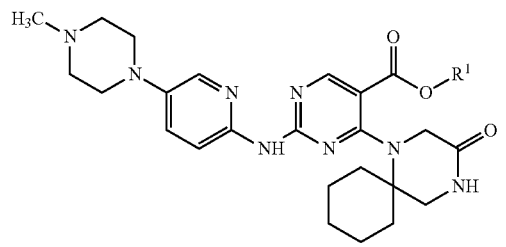

(IV)

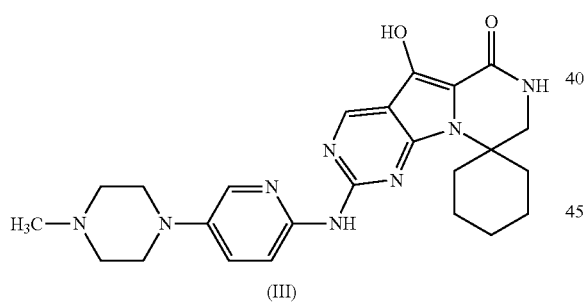

(III)

(d) activating a hydroxyl group of the compound of formula (III) to become a leaving group to afford a compound of formula (II);

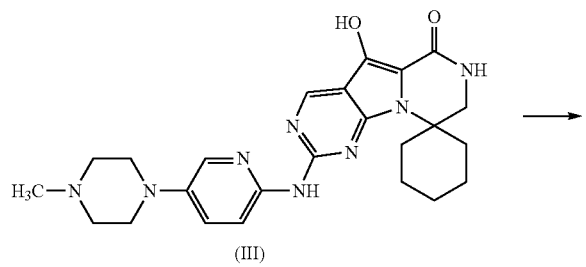

(III)

-continued

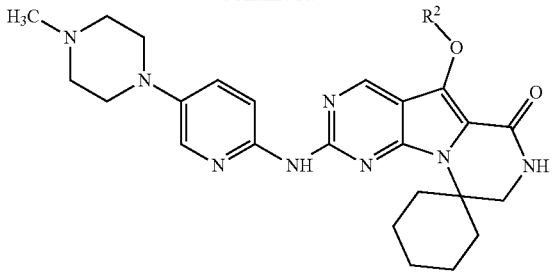

(II)

(e) conducting a reductive elimination of the compound of formula (II) to afford Trilaciclib;

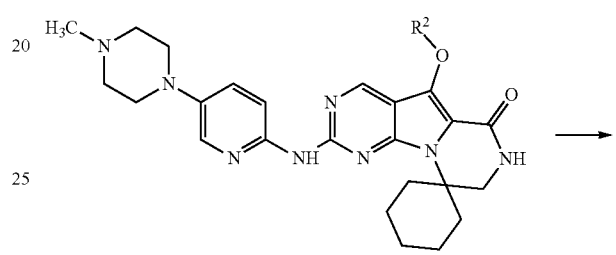

(II)

(I)

wherein $R^1$ is selected from hydrogen or C1~C4 alkyl; $R^2$ is selected from hydrogen, silyl, halo alkyl, —C(O) alkyl, —S(O)$_2$ alkyl, —S(O)$_2$ halo alkyl, —S(O)$_2$ aryl or —S(O)$_2$ aryl-alkyl.

In an embodiment, the reaction in step (a) is to oxidize the thiomethyl group of formula (VII) into a methylsulfonyl group or a methylsulfinyl group corresponding to the compound of formula (VI-1) or formula (VI-2) respectively.

In an embodiment, the oxidizing agent used in the step (a) is selected from the group consisting of oxone, hydrogen peroxide, meta-chloroperoxybenzoic acid (mCPBA), sodium hypochlorite and sodium chlorite. The oxidizing agent (also known as an oxidant, oxidizer, electron recipient, or electron acceptor) mentioned above is a chemical species in a redox chemical reaction that gains (or accepts or receives) an electron from a reducing agent (called the reductant, reducer, or electron donor). The oxidation state, which describes the degree of loss of electrons, of the oxidizing agent decreases after oxidizing agent another substance.

In an embodiment, the step (a) is conducted in a solvent. The solvent mentioned above is a substance that dissolves a solute, resulting in a solution, and is usually a liquid. More particularly, for example, the solvent used for the oxidation reaction provided herein includes, but are not limited to, acetonitrile, tetrahydrofuran, dimethylformamide, dimethyl sulfoxide, water, dioxane, a mixture of water and acetonitrile, a mixture of water and tetrahydrofuran or a mixture of water and dioxane.

In an embodiment, the step (a) is carried out at a temperature of –20 to 80° C. More particularly, the temperature of, for example, –20 to 80° C., –10 to 80° C., 0 to 80° C., 10 to 80° C., 20 to 80° C., 30 to 80° C., 40 to 80° C., 50 to 80° C., 60 to 80° C., 70 to 80° C., –20 to 70, –10 to 70, 0 to 70° C., 10 to 70° C., 20 to 70° C., 30 to 70° C., 40 to 70° C., 50 to 70° C., 60 to 70° C., –20 to 60° C., –10 to 60° C., 0 to 60° C., 10 to 60° C., 20 to 60° C., 30 to 60° C., 40 to 60° C., 50 to 60° C., –20 to 50° C., –10 to 50° C., 0 to 50° C., 10 to 50° C., 20 to 50° C., 30 to 50° C., 40 to 50° C., –20 to 40° C., –10 to 40° C., 0 to 40° C., 10 to 40° C., 20 to 40° C., 30 to 40° C., –20 to 30° C., –10 to 30° C., 0 to 30° C., 10 to 30° C., 20 to 30° C., –20 to 20° C., –10 to 20° C., 0 to 20° C., 10 to 20° C., –20 to 10° C., –10 to 10° C., 0 to 10° C., –20 to 0° C., –10 to 0° C. or –20 to –10° C.

In an embodiment, the oxidizing agent is added slowly to the reaction mixture, and the time of oxidizing agent addition is about 20 to 180 minutes. More particularly, the oxidizing agent is added for, for example, 20 to 160 minutes, 30 to 150 minutes, 40 to 120 minutes, 50 to 100 minutes, 60 to 80 minutes.

In an embodiment, the reaction in step (b) is a nucleophilic substitution reaction of the compound of formula (V) and the compound of formula (VI-1) or (VI-2) under a strong alkali to afford a compound of formula (IV).

The nucleophilic substitution reaction mentioned above is a class of chemical reactions in which a nucleophile (known as an electron-rich chemical species) replaces a functional group within another electrophile (known as an electron-deficient chemical species).

In an embodiment, the strong alkali mentioned above is alkali metal hexamethyldisilazane (alkali metal HMDS); more particularly, the strong alkali provided herein includes, but are not limited to, lithium hexamethyldisilazane (LiHMDS), sodium hexamethyldisilazane (NaHMDS) or potassium hexamethyldisilazane (KHMDS).

In an embodiment, the solvent used in the step (b) is selected from the group consisting of tetrahydrofuran, 1,4-dioxane and toluene. More particularly, for example, the solvent used for the nucleophilic substitution provided herein includes, but are not limited to, tetrahydrofuran, 1,4-dioxane, toluene, a mixture of tetrahydrofuran and 1,4-dioxane, a mixture of tetrahydrofuran and toluene, a mixture of 1,4-dioxane and toluene or a mixture of tetrahydrofuran, 1,4-dioxane and toluene.

In an embodiment, the step (b) is carried out at a temperature of –40 to 60° C. More particularly, the temperature of, for example, –40 to 60° C., –10 to 60° C., 0 to 60° C., 10 to 60° C., 20 to 60° C., 30 to 60° C., 40 to 60° C., 50 to 60° C., –20 to 50° C., –10 to 50° C., 0 to 50° C., 10 to 50° C., 20 to 50° C., 30 to 50° C., 40 to 50° C., –20 to 40° C., –10 to 50° C., 0 to 50° C., 10 to 50° C., 20 to 50° C., 30 to 50° C., 40 to 50° C., –20 to 40° C., –10 to 40° C., 0 to 40° C., 10 to 40° C., 20 to 40° C., 30 to 40° C., –20 to 30° C., –10 to 30° C., 0 to 30° C., 10 to 30° C., 20 to 30° C., –20 to 20° C., –10 to 20° C., 0 to 20° C., 10 to 20° C., –20 to 10° C., 0 to 20° C., 10 to 20° C., −20 to 10° C., −10 to 10° C., 0 to 10° C., –20 to 0° C., –10 to 0° C., –20 to –10° C.

In an embodiment, the equivalent of the alkali metal HMDS is 1.0 to 20 equiv. More particularly, the equivalent of the reagent is, for example, 1 to 20 equiv., 2 to 20 equiv., 3 to 20 equiv., 4 to 20 equiv., 5 to 20 equiv., 6 to 20 equiv., 7 to 20 equiv., 8 to 20 equiv., 9 to 20 equiv., 1 to 19 equiv., 2 to 19 equiv., 3 to 19 equiv., 4 to 18 equiv., 5 to 18 equiv., 6 to 17 equiv., 7 to 17 equiv., 8 to 17 equiv., 9 to 16 equiv., 10 to 16 equiv., 11 to 15 equiv., 12 to 15 equiv., 13 to 15 equiv.

In an embodiment, the reaction in step (c) is an intramolecular cyclization of the ester group of the compound of formula (IV) in presence of a base to afford a compound of formula (III).

In an embodiment, the base mentioned above provided herein includes, but are not limited to, lithium hydroxide, sodium hydroxide, magnesium hydroxide, aluminum hydroxide, sodium methoxide, N,N-diisopropylethylamine (DIPEA), 4-Dimethylaminopyridine (DMAP), 1,4-diazabicyclo[2.2.2]octane (DABCO), triethylamine (TEA), 1,8-diazabicyclo[5.4.0]undec-7-ene (DBU), potassium tert-butoxide (tBuOK) and sodium tert-butoxide (tBuONa).

In an embodiment, the intramolecular cyclization is carried out at a temperature of 50 to 100° C. More particularly, the temperature of, for example, 50 to 100° C., 60 to 100° C., 70 to 100° C., 80 to 100° C., 90 to 100° C., 50 to 90° C., 60 to 90° C., 70 to 90° C., 80 to 90° C., 50 to 80° C., 60 to 80° C., 70 to 80° C., 50 to 70° C., 60 to 70° C., 50 to 60° C.

In an embodiment, the intramolecular cyclization is carried out for 8 to 72 hours. More particularly, the intramolecular cyclization is carried out for, for example, 8 to 72 hours, 16 to 72 hours, 24 to 72 hours, 32 to 72 hours, 40 to 72 hours, 48 to 72 hours, 56 to 72 hours, 64 to 72 hours, 8 to 64 hours, 16 to 64 hours, 24 to 64 hours, 32 to 64 hours, 40 to 64 hours, 48 to 64 hours, 56 to 64 hours, 8 to 56 hours, 16 to 56 hours, 24 to 56 hours, 32 to 56 hours, 40 to 56 hours, 48 to 56 hours, 8 to 48 hours, 16 to 48 hours, 24 to 48 hours, 32 to 48 hours, 40, to 48 hours, 8 to 40 hours, 16 to 40 hours, 24 to 40 hours, 32 to 40 hours, 8 to 32 hours, 16 to 32 hours, 24 to 32 hours, 8 to 24 hours, 16 to 24 hours, 8 to 16 hours.

In an embodiment, the compound of formula (III) after step (c) provided herein may optionally be isolated by, includes, but are not limited to, filtration, decantation, extraction, distillation, evaporation, chromatography, precipitation, concentration, crystallization, centrifugation, or recrystallization.

In an embodiment, the compound of formula (III) may be dried using conventional techniques, includes, but are not limited to, drying, drying under vacuum, spray drying, air drying or agitated thin film drying.

In an embodiment, the reaction in step (d) is to activate a hydroxyl group of formula (III) to become a good leaving group by a reagent to afford the compound of formula (II).

In an embodiment, the aforesaid reagent provided herein includes, but are not limited to, p-toluensulfonyl chloride, p-toluensulfonyl anhydride, trifloromethane sulfonylchloride, trifloromethane sulfonic anhydride, methane sulfonyl chloride and methane sulfonyl anhydride.

In an embodiment, the equivalent of the reagent is 1.0 to 20 equiv. More particularly, the equivalent of the reagent is, for example, 1 to 20 equiv., 2 to 20 equiv., 3 to 20 equiv., 4 to 20 equiv., 5 to 20 equiv., 6 to 20 equiv., 7 to 20 equiv., 8 to 20 equiv., 9 to 20 equiv., 1 to 19 equiv., 2 to 19 equiv., 3 to 19 equiv., 4 to 19 equiv., 5 to 19 equiv., 6 to 19 equiv., 7 to 19 equiv., 8 to 19 equiv., 1 to 18 equiv., 2 to 18 equiv., 3 to 18 equiv., 4 to 18 equiv., 5 to 18 equiv., 6 to 18 equiv., 7 to 18 equiv., 1 to 17 equiv., 2 to 17 equiv., 3 to 16 equiv., 4 to 15 equiv., 5 to 14 equiv., 6 to 13 equiv., 1 to 12 equiv., 2 to 11 equiv., 3 Substitute Specification Clean to 10 equiv., 4 to 9 equiv., 5 to 8 equiv., 1 to 7 equiv., 2 to 6 equiv., 3 to 5 equiv., 4 to 5 equiv., 1 to 4 equiv., 2 to 4 equiv., 3 to 4 equiv., 1 to 3 equiv., 2 to 3 equiv., 1 to 2 equiv.

In an embodiment, the solvent provided herein includes, but are not limited to, dichloromethane, dimethylformamide, acetonitrile, tetrahydrofuran.

In an embodiment, the step (d) is carried out at a temperature of −20 to 90° C. More particularly, the temperature of, for example, −20 to 90° C., −10 to 90° C., 0 to 90° C., 10 to 90° C., 20 to 90° C., 30 to 90° C., 40 to 90° C., 50 to 90° C., 60 to 90° C., 70 to 90° C., 80 to 90° C., −20 to 80° C., −10 to 80° C., 0 to 80° C., 10 to 80° C., 20 to 80° C., 30 to 80° C., 40 to 80° C., 50 to 80° C., 60 to 80° C., 70 to 80° C., −20 to 70° C., −10 to 70° C., 0 to 70° C., 10 to 70° C., 20 to 70° C., 30 to 70° C., 40 to 70° C., 50 to 70° C., 60 to 70° C., −20 to 60° C., −10 to 60° C., 0 to 60° C., 10 to 60° C., 20 to 60° C., 30 to 60° C., 40 to 60° C., 50 to 60° C., −20 to 50° C., −10 to 50° C., 0 to 50° C., 10 to 50° C., 20 to 50° C., 30 to 50° C., 40 to 50° C., −20 to 40° C., −10 to 40° C., 0 to 40° C., 10 to 40° C., 20 to 40° C., 30 to 40° C., −20 to 30° C., −10 to 30° C., 0 to 30° C., 10 to 30° C., 20 to 30° C., −20 to 20° C., −10 to 20° C., 0 to 20° C., 10 to 20° C., −20 to 10° C., −10 to 0° C., 0 to 10° C., −20 to 0° C., −10 to 0° C., −20 to −10° C.

In an embodiment, the step (d) is carried out for 1 to 30 hours; more particularly, for example, for 1 to 30 hours, 5 to 30 hours, 10 to 30 hours, 15 to 30 hours, 20 to 30 hours, 25 to 30 hours, 1 to 25 hours, 5 to 25 hours, 10 to 25 hours, 15 to 25 hours, 20 to 25 hours, 1 to 20 hours, 5 to 20 hours, 10 to 20 hours, 15 to 20 hours, 1 to 15 hours, 5 to 15 hours, 10 to 15 hours, 1 to 10 hours, 5 to 10 hours, 1 to 5 hours.

In an embodiment, the compound of formula (II) may optionally be isolated by, but are not limited to, filtration, decantation, extraction, distillation, evaporation, chromatography, precipitation, concentration, crystallization, centrifugation, or recrystallization.

In an embodiment, the compound of formula (II) may be dried using conventional techniques, includes, but are not limited to, drying, drying under vacuum, spray drying, air drying or agitated thin film drying.

In an embodiment, the reaction in step (e) is a reductive elimination of the compound of formula II in presence of a palladium catalyst with a reducing agent to afford Trilaciclib of formula (I).

In an embodiment, the palladium catalyst mentioned above provided herein, but is not limited to, a Pd/C catalyst, a tetrakis(triphenylphosphine)palladium (0) catalyst, a palladium acetate, a palladium chloride catalyst, a trans-dichlorobis(acetonitrile)palladium (II) catalyst, a 1,1-bis(diphenylphosphino)ferrocene)dichloropalladium-dichloromethane (1:1) catalyst, a 1,1'-bis(diphenylphosphino)ferrocene)dichloropalladium, tris(dibenzyllideneacetone)dipalladium catalyst, bis(triphenylphosphine)palladium (II) dichloride catalyst.

In an embodiment, the reducing agent provided herein, but is not limited to, for example, hydrogen gas, triethyl silane, trimethyl silane, ammonium formate and formic acid.

In an embodiment, the solvent used in the step (e) is selected from a group consisting of alcohols, ethers, esters and other solvents. More particularly, the solvent provided herein, but is not limited to, for example, methanol, ethanol, propanol, isopropanol, n-butanol, 2-butanol, t-butanol, tetrahydrofuran, 1,4-dioxane, diisopropylether, methyl t-butyl ether, ethyl acetate, butyl acetate, dimethyl sulfoxide, N,N-dimethyl formamide, acetonitrile and N,N-dimethyl acetamide.

In another aspect, the present invention provides a compound of formula (II),

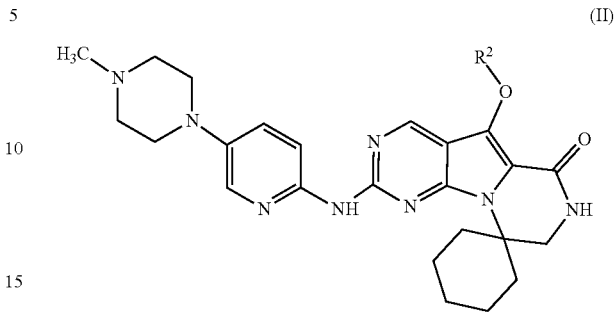

(II)

wherein $R^2$ is selected from hydrogen, silyl, halo alkyl, —C(O) alkyl, —S(O)$_2$ alkyl, —S(O)$_2$ halo alkyl, —S(O)$_2$ aryl or —S(O)$_2$ aryl-alkyl. More particularly, $R^2$ provided herein, but is not limited to, for example, tosylate (Ts), triflate (Tf), Mesyl (Ms).

In another aspect, the present invention provides a compound of formula (III), which is 5'-hydroxy-2'-((5-(4-methylpiperazin-1-yl)pyridine-2-yl)amino)-7',8'-dihydro-6'H-spiro[cyclohexane-1,9'-pyrazino[1',2':1,5]pyrrolo[2,3-d]pyrimidin]-6'-one.

In another aspect, the present invention provides a compound of formula (IV),

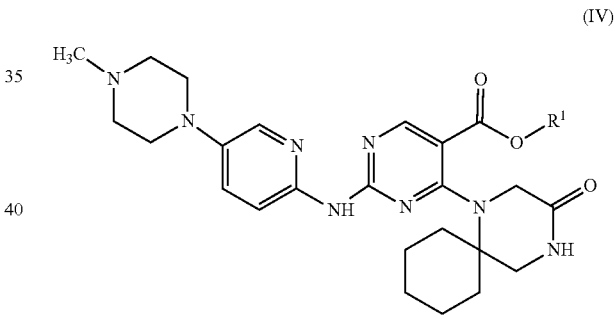

(IV)

wherein $R^1$ is selected from hydrogen or C1-C4 alkyl, aryl.

Examples

In this section, the contents of the present invention will be described in detail through the following examples. These examples are for illustration only, and those skilled in the art can easily think of various modifications and changes. As such, various embodiments of the present invention will be described in detail below, while the invention is not limited to said various embodiments listed in this specification Methods and Material Chromatographic purity is determined by the high performance liquid chromatography (HPLC) using Waters Model 2489. The column used is an InertSustain C18-5 µm (250*4.6 mm).

[Preparation of the Compound of Formula (VI-1) or (VI-2)]

The 3L three-necked round bottom flask was charged with the compound of formula (VII) (20 g, 54.8 mmol) and the solvent ACN (400 mL) and then stirred for 10 min. The solution of the oxidizing agent oxone (84.2 g, 274 mmol) in purified water (400 mL) was stirred for 10 minutes to form a clear solution. The oxone solution was slowly added to the compound of formula (VII) solution and the mixture was stirred at room temperature for 4.5 hours. Then, 1600 mL purified water was added and stirred at room temperature for 1 hour. The mixture was filtered through filter paper and the wet cake was washed with purified water (200 mL*3 times) until the pH of mother liquid was equal to or larger than 5. The wet cake was dried at 60° C. in hot air oven for 8 to 16 hours to obtain the compound of formula (VI-1) or (VI-2) (17.475 g, 80% yields, HPLC purified equal to or larger than 95%) as a white solid.

$^1$H NMR (400 MHz, DMSO-d) δ ppm 1.32 (t. J=7.2 Hz, 3H) 1.36-1.60 (m, 8H) 2.89-3.05 (m, 2H) 3.34 (s, 3H) 3.44 (s, 2H) 3.60 (s, 2H) 4.35 (q, J=7.2 Hz, 2H) 8.22 (s, 1H) 8.81 (s, 1H). $^{13}$C NMR (100 MHz, DMSO-d) δ ppm 13.8, 21.7, 24.7, 29.9, 38.9, 45.7, 53.6, 61.4, 61.7, 114.1, 159.9, 161.0, 163.3, 164.0, 166.9. LCMS (ESI) 397 (M+H).

[Preparation of the Compound of Formula (IV)]

The 500 mL three-necked round bottom flask was charged with the compound of formula (VI-1) or (VI-2) (4 g, 10.1 mmol), the compound of formula (V) (2 g, 10.4 mmol) and the solvent THF (200 mL). The mixture was degassed and refilled with nitrogen for 3 times. The mixture was cooled to −10° C. and was added LiHMDS (1M, in THF, 100 mL) under nitrogen. The mixture was stirred at room temperature for 5 hours. Then, the mixture was cooled to 0 to 5° C. and was added 0.5 M NaCl (80 mL). The heterogeneous reaction mixture was stirred at room temperature for 1 hour and then filtered through filter paper.

The cake was washed with purified water (40 mL*3 times). After drying the wet cake at 60° C. for 16 hours, the compound of formula (IV) was obtained (4.107 g, 80% yields, HPLC purity equal to or larger than 96%) as a yellow solid. 1H NMR (400 MHz, DMSO-d) δ ppm 1.29 (t. J=7.2 Hz, 3H) 1.25-1.50 (m., 8H) 2.22 (s, 3H) 2.46 (t. J=4.8, 3.6 Hz, 4H) 2.70-2.84 (m, 2H) 3.13 (t. J=4.8, 3.6 Hz, 4H) 3.40 (bs, 2H) 3.53 (s, 2H) 4.25 (q. J=7.2 Hz, 2H) 7.39 (dd. J=2.8 Hz, 8.8 Hz, 1H) 7.74 (d, J=9.2 Hz, 11H) 7.88 (s, 11H) 8.0 (d, J=2.8 Hz, 11H) 8.64 (s, 11H) 9.72 (s, 1H). $^{13}$C NMR (100 MHz, DMSO-d) δ ppm 14.0, 20.9, 25.2, 31.2, 45.6, 47.1, 48.1, 54.1, 54.3, 57.1, 60.1, 105.4, 124.6, 135.1, 143.2, 143.4, 158.5, 161.8, 164.2, 167.4. LCMS (ESI) 509 (M+H).

[Preparation of the Compound of Formula (III)]

The 2L three-necked round bottom flask was charged with the compound of formula (VI-1) or (VI-2) (10 g, 25.2 mmol), the compound of formula (V) (5 g, 26 mmol) and the solvent THF (200 mL). The mixture was degassed and refilled with nitrogen for 3 times. The mixture was cooled to −10° C. and was added LiHMDS (1M in THF, 125 mL) under nitrogen. The mixture was stirred at room temperature for 5 hours. The mixture was cooled to 0 to 5° C. and was added purified water (200 mL). The mixture was heated to 55 to 60° C. for 12 hours. The mixture was cooled to room temperature and then filtered through filter paper. The cake was washed with purified water (100 mL*3 times). The wet cake was dried at 60° C. for 16 hours to obtain the compound of formula (III) (9.102 g, 78% yields, HPLC purity equal to or larger than 96%) as yellow solid.

$^1$H NMR (400 MHz, DMSO-d) δ ppm 1.20-1.50 (m, 4H) 1.60-1.90 (m, 4H) 2.22 (s, 3H) 2.46 (t. J=4.8, 4H) 2.70-2.84 (m, 2H) 3.10 (t. J=4.8, 4H) 3.38 (s, 2H) 6.85 (s, 2H) 7.36 (dd. J=3.2 Hz, 8.8 Hz, 1H) 7.98 (d, J=3.2 Hz) 8.13 (d, J=9.2 Hz, 1H) 8.51 (s, 1H) 9.1 (s, 1H). $^{13}$C NMR (100 MHz, DMSO-d) δ ppm 22.3, 25.3, 31.1, 45.6, 45.7, 48.0, 48.6, 54.3, 54.5, 57.1, 105.3, 110.1, 112.7, 125.0, 135.4, 142.1, 146.1, 148.8, 160.0, 156.1, 160.9, 162.7. LCMS (ESI) 463 (M+H).

[Preparation of the Compound of Formula (11)]

The 500 mL three-necked round bottom flask was charged with the compound of formula (III) (4 g, 8.65 mmol), p-toluenesulfonyl chloride (8.25 g, 43.28 mmol, 5.0 equiv.) and ACN (80 mL) and then stirred for 10 minutes. Et$_3$N (8.44 mL, 60.55 mmol) was added slowly at room temperature. The mixture was heated to 75 to 80° C. and stirred for 2.5 hours. The mixture was cooled to room temperature and the was added 0.5 M NaHCO$_3$(a$_q$) (80 mL). The mixture was stirred at room temperature for 1 hour and then then filtered through filter paper. The cake was washed with purified water (50 mL*3 times). The wet cake was dried at 60° C. in hot air oven for 12 hours to obtain the compound of formula (II) (4.817 g, 90% yields, HPLC purity equal to or larger than 98%) as a yellow solid.

LCMS (ESI) 617 (M+H).

[Preparation of the Compound of Formula (II)HCl]

The 500 mL three-necked round bottom flask was charged with the compound of formula (II) (4 g, 6.49 mmol), 2N HCl (6.49 mL, 2.0 equiv.) and MeOH (40 mL) and then stirred for 1 hr. The reaction mixture was quenched with acetone (200 mL), then stirred for 1 hr. Filtered and washed acetone. The wet cake was dried at 60° C. in hot air oven for 12 hours to obtain the compound of formula (II) HCl (3.24 g, 72% yields, HPLC purity equal to or larger than 98%) as a yellow solid.

$^1$H NMR (400 MHz, D20) δ ppm 0.95-1.47 (m, 5H) 1.47-1.80 (m, 3H), 2.25-2.48 (m, 5H) 3.01 (s, 3H) 3.10-3.40 (m, 6H) 3.74 (dd. J=11.6, 34.8 Hz, 4H) 7.23 (d, J=6.8 Hz, 3H) 7.38 (d, J=6.8 Hz, 2H) 7.52 (s, 1H) 7.93 (bs 1H) 8.2 (s, 1H). $^{13}$C NMR (100 MHz, DMSO-d) δ ppm 21.1, 22.0, 24.6, 31.8, 42.9, 45.0, 45.7, 52.8, 61.4, 108.2, 116.0, 119.3, 127.6, 128.3, 128.7, 130.0, 141.0, 143.0, 146.7, 148.0, 150.5, 152.9, 158.7. LCMS (ESI) 617 (M+H).

[Preparation Method 1 of Trilaciclib of Formula (I) Free Base]

The 500 mL three-necked round bottom flask was charged with the compound of formula (II) (2 g, 3.24 mmol), ammonium formate (10.2 g, 162.3 mmol) and 75% EtOH (200 mL). Charged 10% Pd—C(1.6 g) and stirred at 78° C. for 24 hours. Charged 2 N HCl (200 mL) and stirred for 1 hour, then filtered through celite and washed with 2 N HCl. The resulted mother liquor was adjusted pH equal to or larger than 12.0 by 45% NaOH, then stirred for 6 hours. Filtered and washed with water until mother liquor pH equal to or less than 8.0. The cake was dried at 60° C. for 12 hours in hot air oven to obtain Trilaciclib free base (820 mg, 57% yields, HPLC purity equal to or larger than 95%) as yellow solid.

LCMS (ESI) 447 (M+H).

[Preparation Method 2 of Trilaciclib of Formula (I) Free Base]

The 500 mL three-necked round bottom flask was charged with the compound of formula (II) (4 g, 6.49 mmol), tri ethylsilane (4.13 mL, 25.9 mmol) and dimethyl sulfoxide (40 mL). The mixture was degassed and refilled with nitrogen for 3 times. Charged Bis(diphenylphosphino)ferrocene) dichloropalladium-dichloromethane (1:1) (132 mg, 0.16 mmol) then degassed and refilled with nitrogen for 2 times. The resulted heterogeneous solution was stirred at 100° C. for 4 hours. The reaction mixture was quenched with NaOH aq solution. Stirred for 30 minutes, then filtered and washed with water to obtained as crude Trilaciclib wet cake. The crude cake and 2 N HCl (40 mL) charged into round bottom flask, then charged EtOH (40 mL) and stirred for 1 hour and filtered through celite and washed with 2 N HCl: EtOH (1:1). The mother liquor was adjusted to pH equal to or larger than 11.5 by 45% NaOH solution and stirred for 5 hours. The solids were filtered and washed with water until mother liquor pH equal to or less than 8.0. The cake was dried at 60° C. for 12 hours in hot air oven to obtain Trilaciclib free base (2.6 g, 90% yields, HPLC purity equal to or larger than 97%) as a yellow solid.

[Preparation Method 3 of Trilaciclib of Formula (I) Free Base]

The 500 mL three-necked round bottom flask was charged with the compound of formula (II) (4 g, 6.49 mmol), ammonium formate (4.13 mL, 25.9 mmol) and ethanol (60 mL). The mixture was degassed and refilled with nitrogen for 3 times. Charged Bis(diphenylphosphino)ferrocene) dichloropalladium-dichloromethane (1:1) (132 mg, 0.16 mmol) then degassed and refilled with nitrogen for 2 times. The resulted heterogenous solution refluxed for 6 hours. The reaction mixture was quenched with 2 N HCl (40 mL). Stirred for 30 minutes, then filtered and washed with 2 N HCl: EtOH (1:1). The mother liquor was adjusted to pH equal to or larger than 11.5 by 45% NaOH solution and stirred for 5 hours. The solids were filtered and washed with water until mother liquor pH equal to or less than 8.0. The cake was dried at 60° C. for 12 hours in hot air oven to obtain Trilaciclib free base (2.6 g, 90% yields, HPLC purity equal to or larger than 98%) as a yellow solid.

[Preparation of the Compound of Formula (I) HCl]

To the slurry of the compound of formula (I) (2 gr, 4.4 mmol), was added 10 N aq HCl (mL, xxx mmol) slowly at room temperature, then stirred for 1 hour. The reaction mixture was quenched with acetone (xx mL) and stirred for 1 hour. The solids were filtered and washed with acetone. The cake was dried at 60° C. for 6 hours in hot air oven to obtain Trilaciclib HCl (1.8 g, 77% yields, HPLC purity equal to or larger than 99%) as a yellow solid.

In summary, the effect of the present invention is to provide a protection free synthesis of Trilaciclib with less steps and good yields. The simple process for the preparation of trilaciclib is economical and environmentally friendly, and particularly a process technology suitable for industrial production, and is of great realistic significance on improvement of the economic and social benefits of the drug.

The specific embodiments of the present invention have been disclosed, but it is not intended to limit the present invention. Those with ordinary knowledge in the technical field to which the present invention belongs are capable of understanding. And in the case of deviating from the principle and spirit of the present invention, various changes and modifications can be made to it, so the scope of protection of the present invention should be based on those defined in the scope of the accompanying patent application.

What is claimed is:

1. A method for preparing Trilaciclib of formula (I),

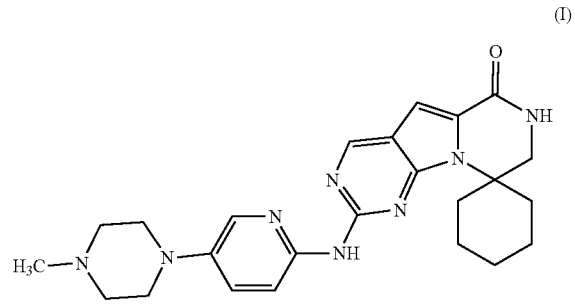 [SMILES: CN1CCN(c2ccc(Nc3ncc4cc5n(c4n3)C3(CCCCC3)CNC5=O)nc2)CC1]

comprising:

(a) oxidizing a compound of formula (VII) to afford a compound of formula (VI-1) or (VI-2);

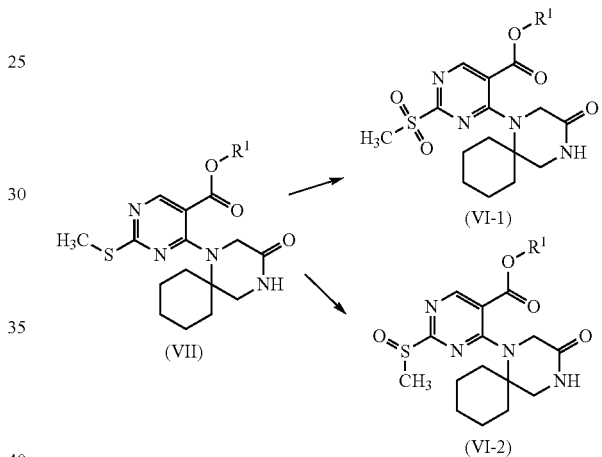

(b) reacting a compound of formula (V) and the compound of formula (VI-1) or (VI-2) under a strong alkali to afford a compound of formula (IV);

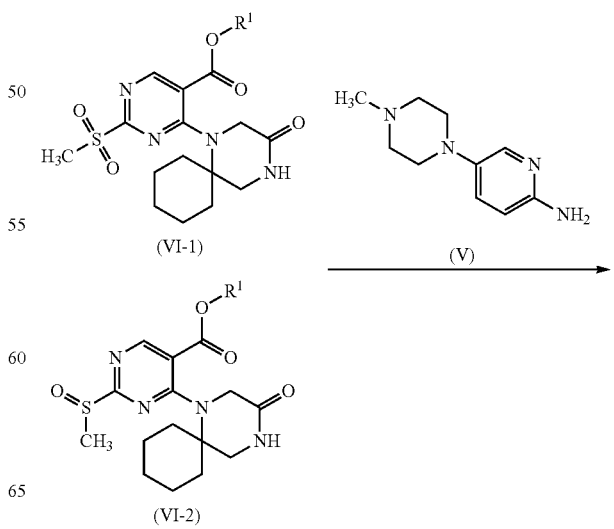

-continued

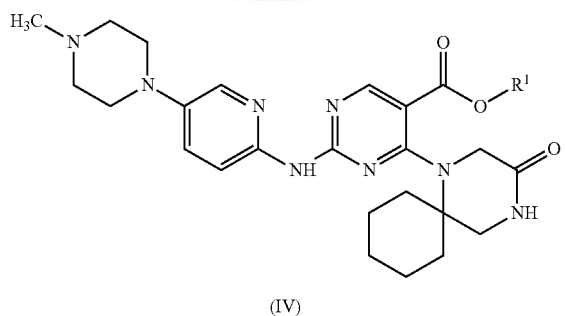

(IV)

(c) conducting an intramolecular cyclization of the compound of formula (IV) in presence of a base to afford a compound of formula (III);

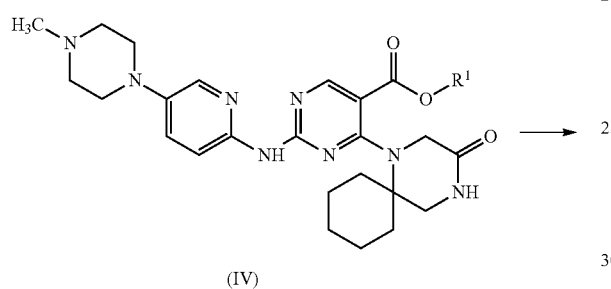

(IV)

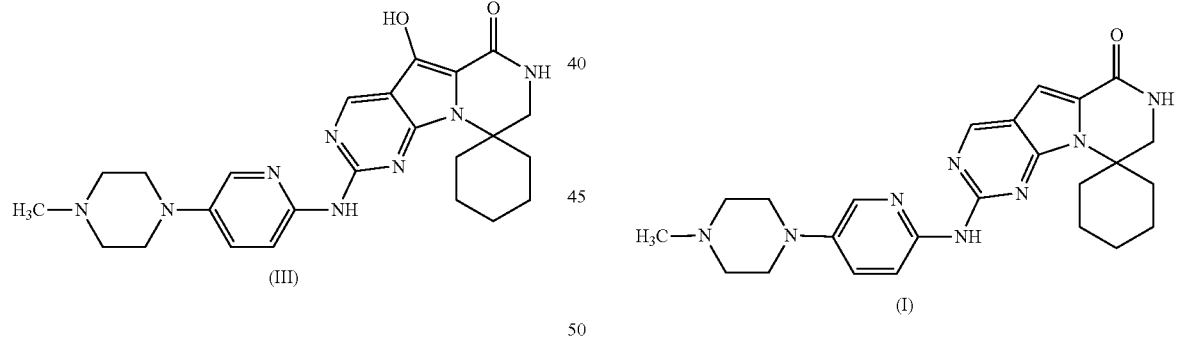

(III)

(d) activating a hydroxyl group of the compound of formula III to become a leaving group to afford a compound of Formula II;

-continued

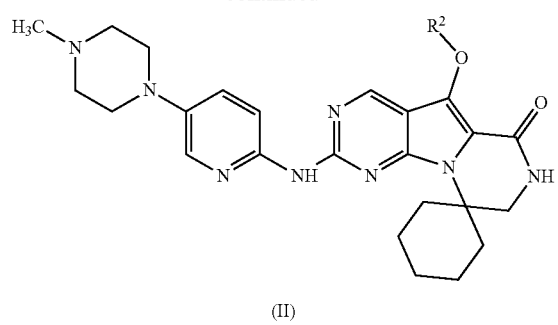

(II)

(e) conducting a reductive elimination of the compound of formula II to afford Trilaciclib of formula (I);

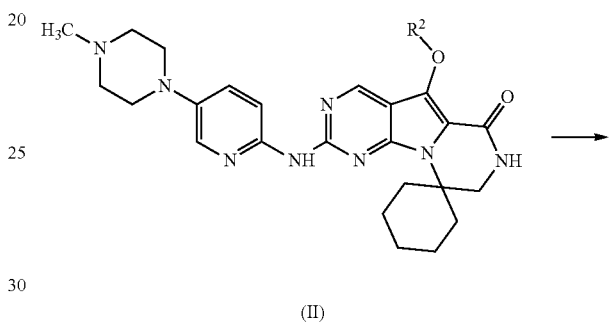

(II)

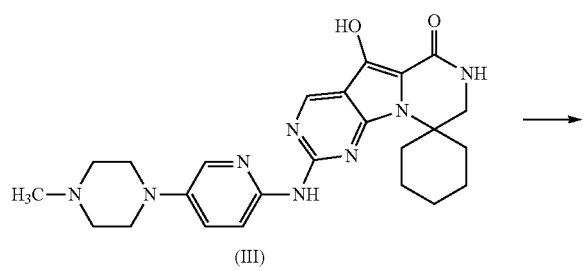

(I)

wherein

R$^1$ is selected from hydrogen or C1~C4 alkyl, aryl;

R$^2$ is selected from hydrogen, silyl, halo alkyl, —C(O) alkyl, —S(O)$_2$ alkyl, —S(O)$_2$ halo alkyl, —S(O)$_2$ aryl or —S(O)$_2$ aryl-alkyl.

2. The method of claim 1, wherein an oxidizing agent used in the step (a) is selected from the group consisting of oxone, hydrogen peroxide, meta-chloroperoxybenzoic acid, sodium hypochlorite and sodium chlorite.

3. The method of claim 1, wherein a solvent used in the step (a) is selected from the group consisting of acetonitrile, tetrahydrofuran, dimethylformamide, dimethyl sulfoxide, water and dioxane.

4. The method of claim 1, wherein the step (a) is carried out at a temperature of −20 to 80° C.

5. The method of claim 1, wherein the strong alkali in the step (b) is alkali metal hexamethyldisilazane.

6. The method of claim 5, wherein the alkali metal hexamethyldisilazane is selected from a group consisting of lithium hexamethyldisilazane, sodium hexamethyldisilazane and potassium hexamethyldisilazane.

7. The method of claim 1, wherein a solvent used in the step (b) is selected from a group consisting of tetrahydrofuran, 1,4-dioxane and toluene.

8. The method of claim 1, wherein the step (b) is carried out at a temperature of −40 to 60° C.

9. The method of claim 1, wherein the base used in the step (c) is selected from a group consisting of lithium hydroxide, sodium hydroxide, magnesium hydroxide, aluminum hydroxide, sodium methoxide, N,N-diisopropylethylamine, 4-dimethylaminopyridine, 1,4-diazabicyclo[2.2.2]octane, triethylamine, 1,8-diazabicyclo[5.4.0]undec-7-ene, potassium tert-butoxide and sodium tert-butoxide.

10. The method of claim 1, wherein the intramolecular cyclization in the step (c) is carried out at a temperature of 50 to 100° C.

11. The method of claim 1, wherein a reagent used to activate the hydroxyl group in the step (d) is selected from the group consisting of p-toluensulfonyl chloride, p-oluensulfonyl anhydride, trifloromethane sulfonylchloride, trifloromethane sulfonic anhydride, methane sulfonyl chloride and methane sulfonyl anhydride.

12. The method of claim 11, wherein the equivalent of the reagent is 1.0 to 20 equiv.

13. The method of claim 1, wherein a solvent used in the step (d) is selected from a group consisting of dichloromathane, dimethylformamide, acetonitrile and tetrahydrofuran.

14. The method of claim 1, wherein the activation of hydroxyl group in the step (d) is carried out at a temperature of −20 to 90° C.

15. The method of claim 1, wherein the reductive elimination in the step (e) is carried out in presence of a palladium catalyst with a reducing agent.

16. The method of claim 15, wherein the palladium catalyst is selected from a group of 10% Pd/C, tetrakis(triphenylphosphine)palladium (0), palladium acetate, palladium chloride, trans-dichlorobis(acetonitrile)palladium (II), 1,1-bis(diphenylphosphino)ferrocene)dichloropalladium-dichloromethane (1:1), 1,1'-bis(diphenylphosphino)ferrocene)dichloropalladium, tris(dibenzyllideneacetone)dipalladium, and bis(triphenylphosphine)palladium (II) dichloride.

17. The method of claim 16, wherein the reducing agent is selected from a group consisting of hydrogen gas, triethyl silane, trimethyl silane, ammonium formate and formic acid.

18. The method of claim 1, wherein the solvent used in the step (e) for the reductive elimination is selected from a group consisting of alcohols, ethers and esters.

19. A compound of formula (II),

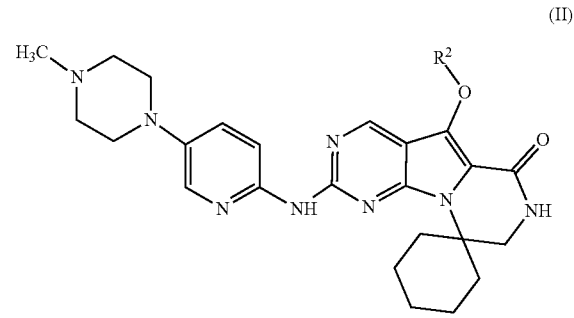

wherein R² is selected from hydrogen, silyl, halo alkyl, —C(O) alkyl, —S(O)₂ alkyl, —S(O)₂ halo alkyl, —S(O)₂ aryl or —S(O)₂ aryl-alkyl.

20. A compound of formula (III),

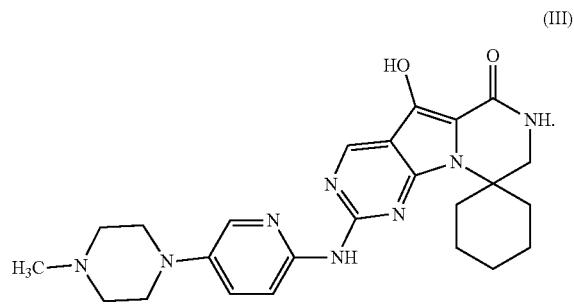 [SMILES: CN1CCN(c2ccc(Nc3ncc4c(O)c5n(c4n3)C3(CCCCC3)CNC5=O)nc2)CC1]

21. A compound of formula (IV),

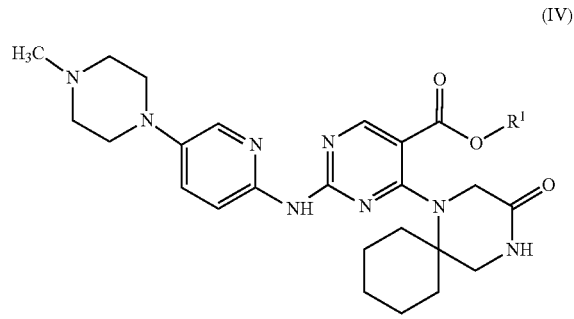

wherein R¹ is selected from hydrogen or C1~C4 alkyl.

* * * * *